United States Patent [19]

Hannah

[11] 4,256,135
[45] Mar. 17, 1981

[54] HIGH FLOW LINED VALVE FOR MEDICAL APPLICATIONS

[75] Inventor: Richard E. Hannah, Spring Grove, Ill.

[73] Assignee: Baxter Travenol Laboratories, Inc., Deerfield, Ill.

[21] Appl. No.: 21,094

[22] Filed: Mar. 16, 1979

[51] Int. Cl.³ .............................................. F16K 5/02
[52] U.S. Cl. .............................. 137/375; 137/625.47; 128/762
[58] Field of Search .......................... 137/375, 625.47; 128/761, 762

[56] References Cited

U.S. PATENT DOCUMENTS

| | | | |
|---|---|---|---|
| 2,621,886 | 12/1952 | Mueller | 137/625.47 |
| 2,832,562 | 4/1958 | Myers | 251/310 X |
| 3,157,195 | 11/1964 | McIntosh et al. | 137/375 |
| 3,227,174 | 1/1966 | Yost | 137/375 |
| 3,337,182 | 8/1967 | Roy, Sr. | 137/375 X |
| 4,000,649 | 1/1977 | Hanifl | 128/762 |
| 4,095,589 | 6/1978 | Manschot et al. | 128/762 |

Primary Examiner—Arnold Rosenthal
Attorney, Agent, or Firm—Paul Flattery; John Caruso; Gary McFarron

[57] ABSTRACT

Improved valves for use within medical devices include a valve body having a plurality of fluid-passing openings, a resilient liner having raised portions defining flow paths, and a plug having a configuration generally complementary to that of the liner, at least a portion of the plug generally overlying the liner for maintaining raised portions of the liner in sealing engagement with the valve body in a manner that enhances valve integrity as to leakage while simultaneously improving valve operation by providing easy rotation of the plug and liner with respect to the valve body. The in-use illustrated embodiment of the valve is on a urine drainage device, the valve being interposed between a relatively rigid urine flow monitoring and measuring chamber and a flexible collection receptacle, the valve permitting flow path selections for retaining urine within the measuring chamber or for flowing urine therefrom into the flexible collection receptacle or through a sampling port.

25 Claims, 11 Drawing Figures

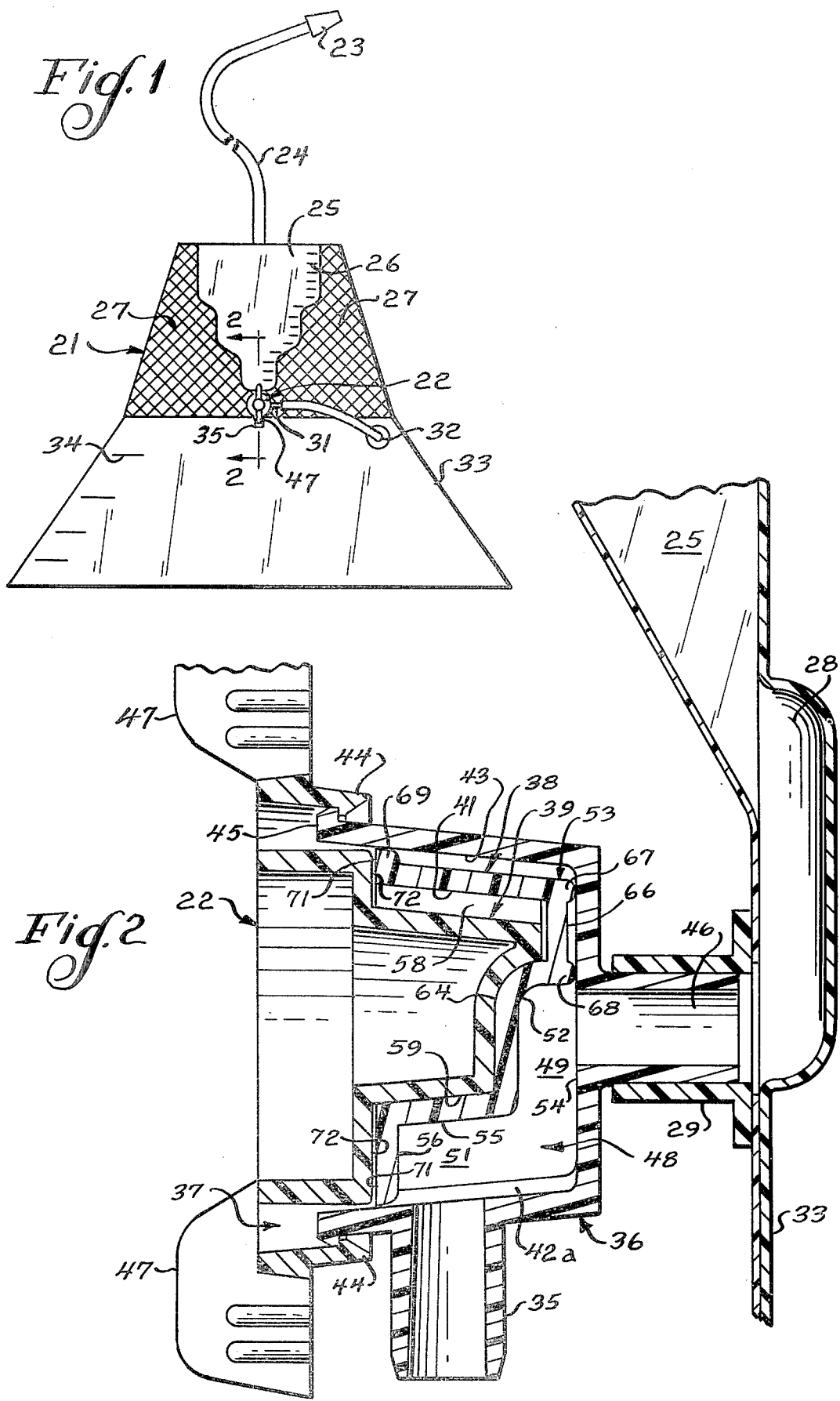

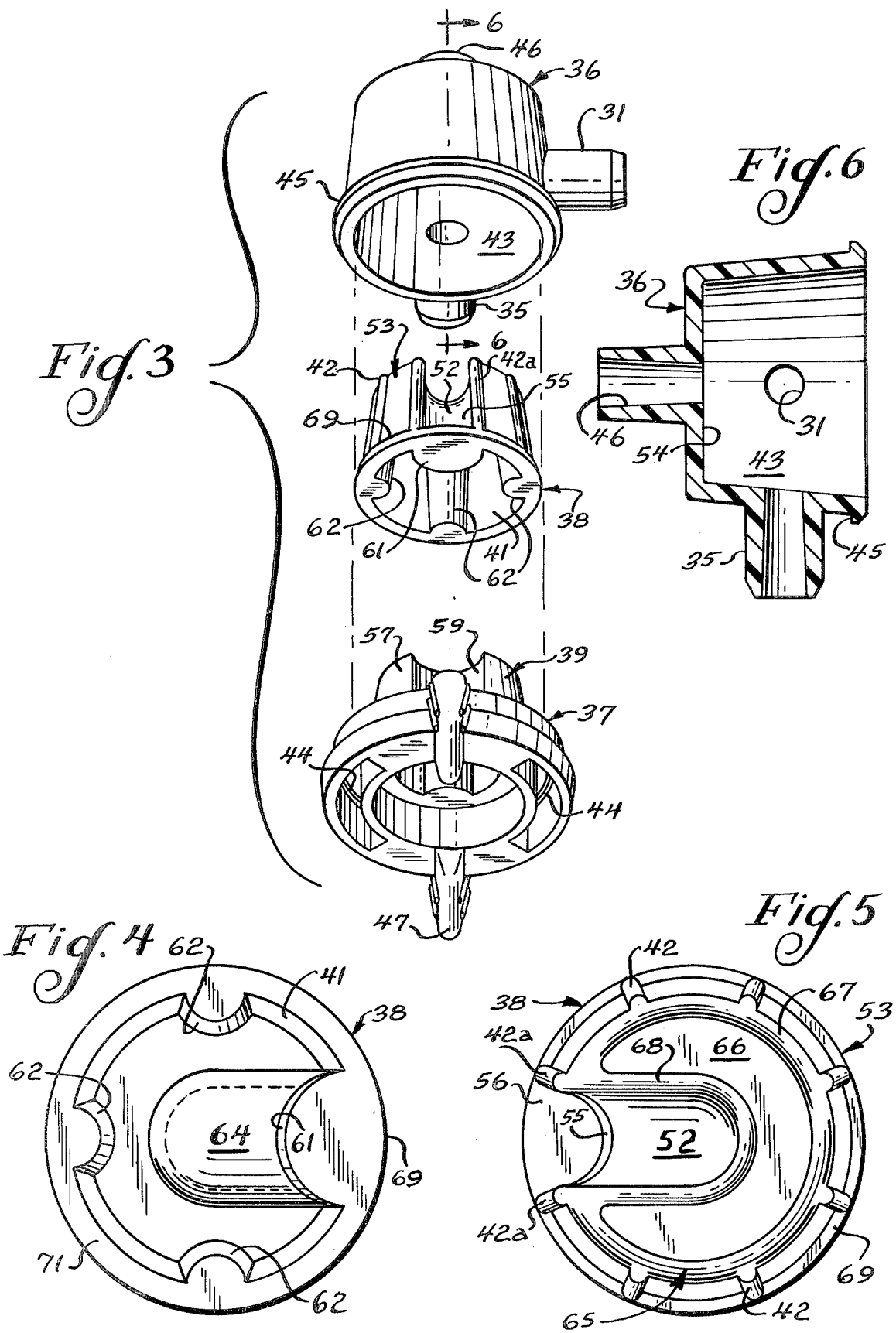

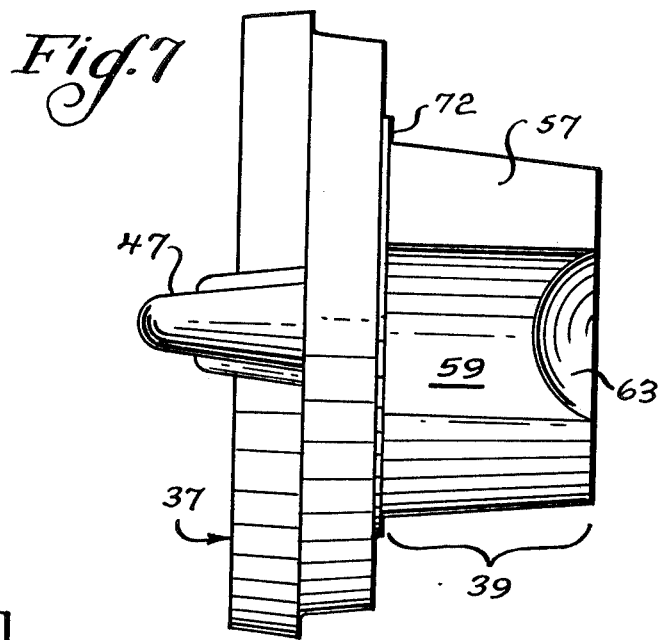
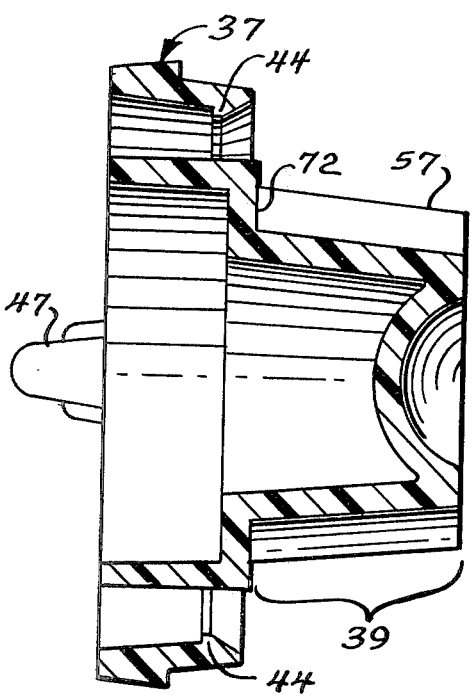
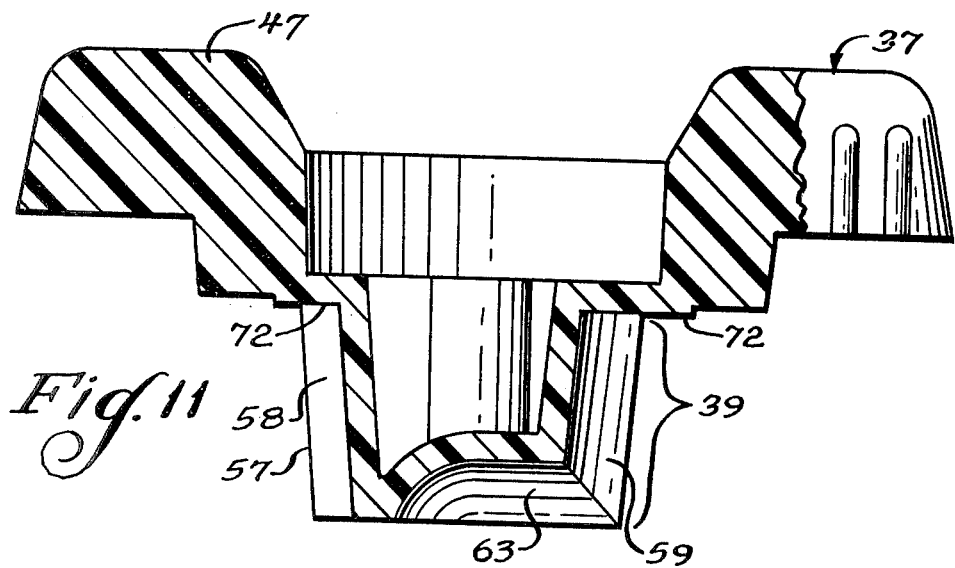

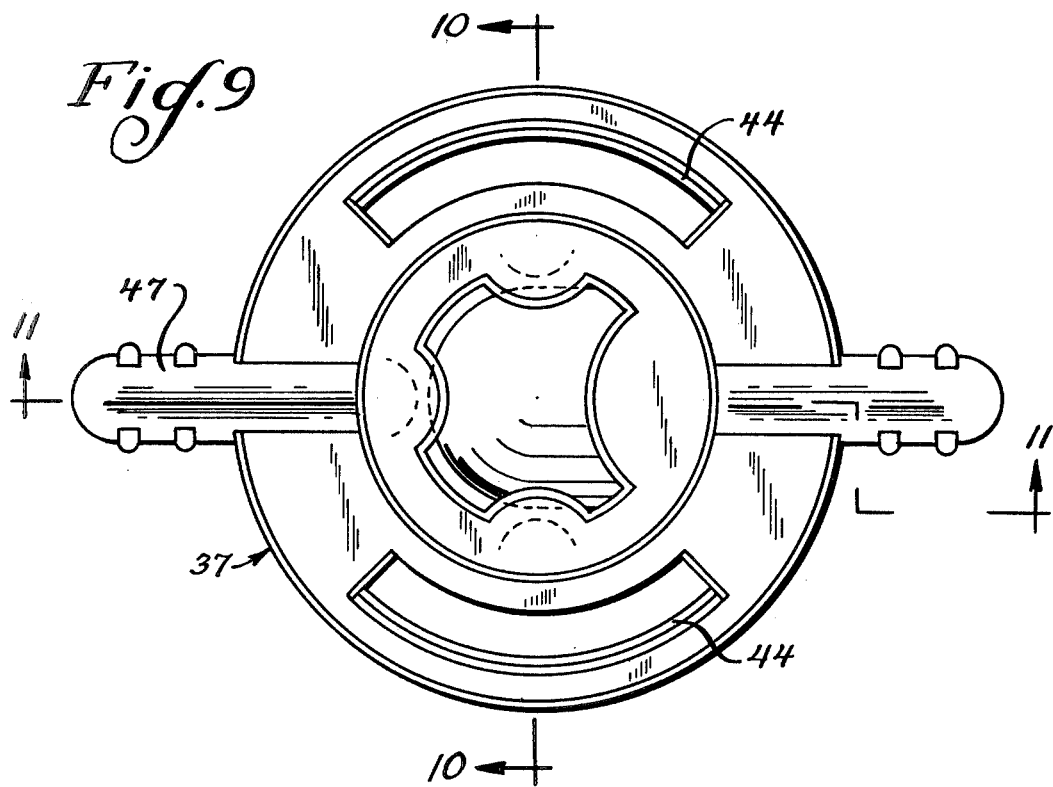
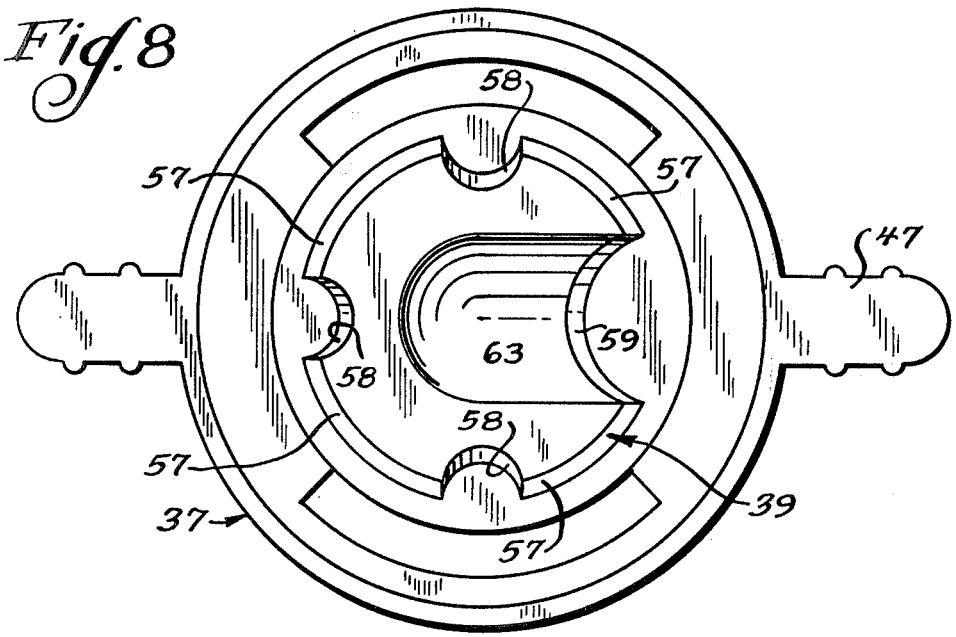

HIGH FLOW LINED VALVE FOR MEDICAL APPLICATIONS

BACKGROUND AND DESCRIPTION OF THE INVENTION

The present invention relates generally to improvements in valves having a plurality of fluid passageways, and more particularly to certain improvements which enhance the sealing integrity and the operational characteristics of valves within medical devices, the illustrated medical device embodiment being a urine drainage device for collecting and monitoring urine discharge from a patient, the device incorporating the improved valve. An important aspect of the improved valve is its inclusion of a resilient liner having raised portions for sealing and for defining a flow path through the valve.

Several different types and structures of valves for use in medical equipment are illustrated in Murphy U.S. Pat. No. 3,048,192 and Burke, et al. U.S. Pat. No. 3,750,704. In general, valves of the unlined type illustrated therein tend to exhibit leaking, which is highly undesirable in medical devices such as those through which urine passes; and such unlined valves also tend to exhibit binding between moving parts of the valve because of the relatively large contact surface areas between those moving parts, this latter condition being aggravated as body fluids seep into the contact areas and begin to dry within the valve. Both problems are particularly troublesome when such valves must be in use for significant lengths of time.

Valves of this unlined type typically include flow directing plugs of substantial depth or wall thickness which render them somewhat rigid, even when made of resilient materials, to the extent that the ability of the sealing surfaces of the plug to be compressed and deformed is not very extensive, and the ability of the plug to seal surfaces in rotatable contact or to wipe those surfaces free of residual fluid clinging to the surfaces of rotation is less than needed to avoid leakage in a consistent manner. Additionally, such plugs have a rotatable contact surface area that is quite extensive, often covering almost the entire internal surface of the valve body, these relatively large surface areas of rotating contact providing an extensive amount of surface area at which frictional forces are developed when attempting to rotate the valve plug with respect to the valve body.

By the present invention, shortcomings of the type just discussed are substantially eliminated. The improved valves according to this invention include a thin-walled liner made of resilient material and having especially positive seating properties and including raised portions for sealing and wiping internal surfaces of the valve while also defining flow paths through the valve. Publications such as Sinkler U.S. Pat. No. 3,061,269 illustrate lined valves in general, the structures thereof and the functions of those structures being significantly different from those of the present invention.

It is accordingly a general object of this invention to provide an improved valve for medical applications.

Another object of the present invention is to provide an improved valve and medical devices having improved valves exhibiting especially superior seating properties.

Another object of the invention is an improved valve assembly having enhanced anti-leakage properties, even when constructed of synthetic plastic materials and when used to pass body fluids, medicaments, or the like.

Another object of the present invention is an improved valve assembly having internal self-wiping properties for reducing frictional build-up caused by residual fluids remaining along rotating surfaces within the valve.

Another object of this invention is an improved valve assembly having thin, resilient raised portions as rotatable contact surfaces with other portions of the valve in order to reduce rotational surface contact and resistance to rotational movement in order to provide an easily working valve.

Another object of the present invention is an improved medical device having a valve exhibiting enhanced anti-leakage properties and reduced build-up of friction that would interfere with ease of movement between various flow paths provided by the device.

These and other objects of the present invention will be apparent from the following detailed description taken in conjunction with the accompanying drawings wherein:

FIG. 1 is an elevational view of an illustrative embodiment of a medical device according to this invention, a urine drainage device;

FIG. 2 is a sectional view taken along line 2—2 of FIG. 1 and illustrating the preferred embodiment of the valve assembly according to this invention and its operative communication with the device depicted in FIG. 1, the valve assembly including a plug member and a body member, with a liner being interposed generally therebetween.

FIG. 3 is an exploded perspective view of the preferred valve assembly, the preferred plug member being located on the bottom of the figure, the body member on the top of the figure, and the preferred liner therebetween;

FIG. 4 is a front view of the liner as shown and as oriented in FIG. 3;

FIG. 5 is a rear view of the liner as shown and as oriented in FIG. 3;

FIG. 6 is a cross-sectional view of the body member, taken along the line 6—6 of FIG. 3;

FIG. 7 is an elevational view of the preferred plug member shown in FIG. 3;

FIG. 8 is a rear view of the member as shown and as oriented in FIG. 3;

FIG. 9 is a front view of the plug member as shown and as oriented in FIG. 3;

FIG. 10 is a cross-sectional view of the preferred plug member, taken along the line 10—10 of FIG. 8; and FIG. 11 is a sectional view of the preferred plug member, taken along the line 11—11 of FIG. 9.

A medical device, generally designated at 21, having a valve assembly, generally identified as 22, is shown in FIG. 1, the illustrative embodiment of device 21 being a urine drainage device or collection system. Typically, a catheter (not shown) will be administered to the patient and it will be in communication with a catheter adapter 23 and its associated conduit 24, which in turn opens into a semirigid measuring chamber 25 having graduations 26 for accurately measuring the volume of urine collection therewithin in order to closely monitor urine discharge of the patient. Often, the measuring chamber 25 will be constructed of bound layers of generally transparent resin film in a manner such that the measuring chamber 25 is a relatively rigid protruding chamber, with the film sheets being somewhat extensively bonded together throughout the area covered by bonding lines 27, to rigidify the film sheets, whereby fluid collects within the measuring chamber 25 but not within the area defined by the bonding lines 27.

Valve assembly 22, as best seen from FIG. 2, is in fluid passing communication with the measuring chamber 25 of device 21 through chamber extension 28, valve assembly 22 being firmly secured to the device 21 by any suitable means, such as a T-shaped flange 29. Valve assembly 22 includes a transfer port 31 (FIGS. 1 and 6) in fluid-passing communication with opening 32 into a flexible fluid collection receptacle or bag 33, including flexible film walls that open to provide an enclosed pocket for receiving urine from the measuring chamber 25, through the valve assembly 22. If desired, graduations 34, which are typically for permitting a somewhat crude determination of the total amount of urine collected therewithin, may be provided on the bag 33. Valve assembly 22 preferably also includes a sampling port 35, provided for the purpose of taking urine samples for analysis thereof. When desired, usually after bag 33 is substantially full, the device 21 can be drained and disposed of.

FIGS. 2 and 3 illustrate the valve assembly 22 in greater detail, the assembly including a rigid valve body member 36 having a plurality of ports, a rigid valve plug member 37, and a resilient liner 38 generally interposed between the body member 36 and the plug member 37. The plug member 37 shown includes a plug portion, generally depicted at 39, which is substantially complementary to an interior surface 41 of the liner 38, and liner 38 has external longitudinal raised portions 42, 42a sealingly engaging an inner surface 43 of the body member 36. Plug member 37 includes one or more locking tabs 44 for engaging an annular retaining flange 45 of the body member 36, the tab 44 and the flange 45 combining to provide means for assembling the plug member 37 onto the body member 36.

Body member 36, plug member 37 and resilient liner 38 are structured to provide a flow path from a valve entry port 46 of the body member 36 to another port, preferably into either the transfer port 31 or into the sampling port 35 as desired, either flow path being attained by moving the selector wings 47 to rotate the plug member 37 and the liner 38 lying thereunder. When neither of these flow paths is desired, the plug member 37 can be aligned so that there is no fluid flow through the valve assembly 22 in order to have a three-way valve. One of the ports can be omitted so as to form a two-way valve, or additional ports (not shown) and flow paths can be provided to form a four-way valve or other multiple-path valve.

With more particular reference to the illustrated three-way valve, FIG. 2 shows a flow path from entry port 46 to sampling port 35, which flow path is selected by aligning a flow channel, generally illustrated by 48, with both the entry port 46 and the sampling port 35. In the preferred from of the illustrated embodiment, the flow channel 48 includes both an inlet channel 49 and a side channel 51, which are illustrated in the drawings as combining to form flow channel 48 that is L-shaped.

Inlet channel 49, which is bounded or defined by a rear indent 52 in the outside surface 53 of the liner 38 and an inner end surface 54 of the body member 36, is in fluid-passing communication with the valve entry port 46 and with the side channel 51, which is defined by side indent 55 in the outside surface 53 of the liner 38 and the inner side surface 43 of the body member 36. In the preferred embodiment illustrated, the rear indent 52 is generally U-shaped along its longitudinal direction, as best seen in FIG. 5, the inner end surface 54 is generally planar, the body member inner side surface 43 is generally frusto-conical, and side indent 55 is generally U-shaped along its longitudinal direction and includes an end surface 56.

In order to provide excellent seating, it is preferred, as shown, that the resilient liner 38 is thin-walled throughout and that the liner interior surface 41 is accordingly generally complementary, typically with the general exception of the various raised portions, to the outside liner surface 53. Excellent seating for superior sealing, wiping, and rotational properties are further enhanced by the plug portion 39 of the plug member 37 having an external surface that is keyed to and generally complementary with the liner interior surface 41.

More particularly, the preferred plug member 37 illustrated in FIGS. 7 through 11 has a plug portion 39 that includes a generally frusto-conical outside surface 57 having a plurality of convex, generally arcuate surface portions that are spaced apart by one or more flutes 58, one of said flutes 58 being a large flute 59 having an external surface of substantially the same size and configuration as the surface of a large spline 61 along the interior surface 41 of the liner 38. Each flute 58 has an external surface of substantially the same size and configuration as the surface of each of one or more splines 62 along the liner interior surface 41, splines 61 and 62 being best seen in FIGS. 3 and 4. Plug portion 39 of the plug member 37 further includes a generally transverse rear flute 63 that is substantially complementary to a generally transverse inside spline 64 of the liner 38.

The respective flutes 58, 59 and 63 of the plug portion 39 are each structured and located such that they closely and complementarily lie over the respective splines 61, 62 and 64 within the liner 38 such that the liner 38 is locked into place within the body member 36 to the extent that the liner 38, especially at its raised portions, is generally compressed into body member 36 to develop firm points of sealing at locations where the resilient liner 38 contacts the body member inner surface 43 and the body member inner end surface 54.

With more particular reference to these compression or contact points, the body member inner end surface 54 contacts the liner 38 along a continuous raised portion, generally designated 65, extending generally along the periphery of an exterior, rear end 66 of the liner 38. The preferred configuration of the continuous raised portion 65 can be best seen in FIG. 5 to include an outer rim or raised portion 67 that generally flanks and terminates at substantially the same location that an inner rim or raised portion 68 terminates such that the outer portion 67 and the inner portion 68 are continous and have no gaps therebetween and such that the inner raised portion 68 provides a sealing surface for the inlet channel 49. Outer raised portion 67 provides a secondary sealing barrier to prevent fluids flowing through inlet channel 49 from seeping out of the valve assembly 22, should some of this fluid make its way over the inner raised portion 68 to the exterior, rear end 66 of the liner 38.

Additional points of sealing or wiping contact are provided by the liner longitudinal raised portions 42, 42a in conjunction with an annular raised portion 69 which extends around the entire periphery of exterior front end 71 of the liner 38. Longitudinal raised portions 42a generally flank the liner side indent 55 and a portion of the end surface 56 to provide a longitudinal sealing surface for the side channel 51 within the valve assembly 22. That portion of the annular raised portion 69 that is co-extensive with the liner end wall 56 seals another portion of the end wall 56 and thus another portion of the side channel 51 for the purpose of preventing flow out of side channel 51 and across the annular raised portion 69 to the plug member 37. Annular raised portion 69 provides especially effective sealing since the liner exterior front end 71 is firmly abutted by an annular bearing surface 72 of the plug member 37.

It will be noted that all contact between the liner 38 and the inner surfaces 43, 54 of the body member 36 is along a raised portion 42, 42a, 65, 67, 68 or 69, to the extent that the contact locations are, in a general sense, lines of contact rather than areas of contact. Sealing contact along narrow surfaces or lines rather than the extensive sealing areas found in valve assemblies not according to this invention provides a minimal contact surface and thus a minimal area along which frictional forces develop when the valve is moved between its flow paths. By these structural relationships, the valve assembly 22 exhibits an especially advantageous ease of operation.

Both body member 36 and plug member 37, although not necessarily made of the same material, should be constructed of relatively rigid materials, such as an injection molded synthetic plastic material, which should be of the type that is acceptable for use in medical devices. The relative rigidity of the body member 36 and plug member 37 can be characterized by its degree of hardness, which is preferably above about shore 90 c, examples being polypropylene, polyvinyl chloride, acrylic materials, and appropriate metals.

Resilient liner 38 should be constructed of a material such that it will complementarily and securely fit over the plug portion 39 and in order that its raised portions will be deformed and exhibit resilience when the liner 38 and plug member 37 are installed within the valve body member 36 which cooperate to provide the sealing and wiping functions of this invention while simultaneously retaining the ease of operation aspect thereof. Typically, such resilient materials will be injection moldable synthetic plastics or elastomers exhibiting a hardness of below about shore 100A, such materials including silicone rubber, natural rubber, polyurethane, and synthetic hydrocarbon elastomers.

It will be apparent to those skilled in this art that the present invention can be embodied in various forms; accordingly, this invention is to be construed and limited only by the scope of the appended claims.

I claim:

1. A lined valve assembly for medical applications, comprising: a valve body member having a plurality of ports passing through the body member; a valve plug member having a plug portion extending into said valve body member; a liner generally interposed between said valve body member and said plug member; resilient means on said liner for providing lines of sealing between said liner and said valve body member and for defining a flow path through the valve assembly, said resilient means including a plurality of resilient raised portions on said liner; said flow path being selectively positioned by movement of said valve plug member with respect to said valve body member; and means for assembling said valve plug member and said valve body member to each other.

2. The valve assembly of claim 1, wherein said plug portion of the valve plug member is generally complementary to said liner.

3. The valve assembly of claim 1, wherein an exterior surface of the plug portion is generally complementary to an interior surface of said liner.

4. The valve assembly of claim 1, wherein said assembling means includes a locking tab on said valve plug member and a retaining flange on said valve body member.

5. The valve assembly of claim 1, wherein said plurality of ports includes an entry port and another port, and said flow path is in communication with said entry port and is selectively in communication with said another port, said selective communication being effected by movement of said valve plug member.

6. The valve assembly of claim 1, wherein said plurality of ports includes an entry port, a transfer port and a sampling port, and said flow path is in communication with said entry port, is selectively in communication with said transfer port, and is selectively in communication with said sampling port.

7. The valve assembly of claim 1, wherein said flow path includes an inlet channel and a side channel.

8. The valve assembly of claim 1, wherein said flow path is generally L-shaped.

9. The valve assembly of claim 1, wherein said flow path is defined by an indent within said liner, said indent being generally flanked by at least a portion of said resilient means.

10. A lined valve assembly for medical applications, comprising: a valve body member having a plurality of ports passing through the body member; a valve plug member having a plug portion extending into said valve body member; a liner generally interposed between said valve body member and said plug member; resilient means on said liner for providing lines of sealing between said liner and said valve body member and for defining a flow path through the valve assembly; said flow path being selectively positioned by movement of said valve plug member with respect to said valve body member; and means for assembling said valve plug member and said valve body member to each other, wherein said resilient means includes a plurality of resilient raised portions, and said flow path is defined by a rear indent in an outside surface of said liner in combination with a side indent in said outside surface of the liner, said rear indent and side indent being bounded by at least some of said resilient raised portions, said flow path being further defined by an inner end surface of the body member and an inner side surface of the body member.

11. The valve assembly of claim 10, wherein said inner end surface of the valve body member is generally planar, said inner side surface of the valve body member is generally frusto-conical, and each of said rear indent and said side indent is generally U-shaped in longitudinal direction.

12. The valve assembly of claim 1, wherein said liner is generally thin-walled throughout.

13. A lined valve assembly for medical applications, comprising: a valve body member having a plurality of ports passing through the body member; a valve plug member having a plug portion extending into said valve body member; a liner generally interposed between said valve body member and said plug member; resilient means on said liner for providing lines of sealing between said liner and said valve body member and for defining a flow path through the valve assembly; said flow path being selectively positioned by movement of said valve plug member with respect to said valve body member; and means for assembling said valve plug member and said valve body member to each other, wherein said resilient means includes a plurality of resilient raised portions, said liner has generally thin walls throughout, said liner has an interior surface and an outside surface having said resilient raised portions, and said interior surface is generally complementary to said outside surface except for said resilient raised portions.

14. A lined valve assembly for medical applications, comprising: a valve body member having a plurality of ports passing through the body member; a valve plug member having a plug portion extending into said valve body member; a liner generally interposed between said valve body member and said plug member; resilient means on said liner for providing lines of sealing between said liner and said valve body member and for defining a flow path through the valve assembly; said flow path being selectively positioned by movement of said valve plug member with respect to said valve body member; and means for assembling said valve plug member and said valve body member to each other, wherein said plug portion of the valve plug member has an outside surface having a flute therein, said flute being generally complementary to a spline along an interior surface of said liner.

15. A lined valve assembly for medical applications, comprising: a valve body member having a plurality of ports passing through the body member; a valve plug member having a plug portion extending into said valve body member; a liner generally interposed between said valve body member and said plug member; resilient means on said liner for providing lines of sealing between said liner and said valve body member and for defining a flow path through the valve assembly; said flow path being selectively positioned by movement of said valve plug member with respect to said valve body member; and means for assembling said valve plug member and said valve body member to each other, wherein said flow path is defined by an indent within said liner, said liner has a generally transverse inside spline generally overlying said flow path indent, said plug portion of the valve plug member has a generally transverse rear flute generally overlying said liner generally transverse inside spline, said liner has generally longitudinal spline along an interior surface thereof, and said plug portion of the valve plug member has an outside surface having a flute generally overlying said spline.

16. A lined valve assembly for medical applications, comprising: a valve body member having a plurality of ports passing through the body member; a valve plug member having a plug portion extending into said valve body member; a liner generally interposed between said valve body member and said plug member; resilient means on said liner for providing lines of sealing between said liner and said valve body member and for defining a flow path through the valve assembly; said flow path being selectively positioned by movement of said valve plug member with respect to said valve body member; and means for assembling said valve plug member and said valve body member to each other, wherein said plug portion of the valve plug member has an outside surface having a plurality of flutes therein, said flutes being generally complementary to a plurality of splines along an interior surface of said liner, one of said splines overlying an indent of said liner, said liner indent defining, in cooperation with said liner resilient means, at least a portion of said flow path.

17. The valve assembly of claim 1, wherein said resilient means is in compressed contact with an inner surface of said valve body member.

18. A lined valve assembly for medical applications, comprising: a valve body member having a plurality of ports passing through the body member; a valve plug member having a plug portion extending into said valve body member; a liner generally interposed between said valve body member and said plug member; resilient means on said liner for providing lines of sealing between said liner and said valve body member and for defining a flow path through the valve assembly; said flow path being selectively positioned by movement of said valve plug member with respect to said valve body member; and means for assembling ssaid valve plug member and said valve body member to each other, wherein said resilient means includes a plurality of raised portions, said raised portions including a plurality of generally longitudinal raised portions, a continuous raised portion extending generally along the periphery of an exterior rear end of said liner, and an annular raised portion along the periphery of an exterior front end of said liner.

19. The valve assembly of claim 1, wherein said valve body member is constructed of a rigid material, said valve plug member is constructed of a rigid material, and said liner is constructed of a resilient material having a hardness value less than the hardness value of both said body member material and said plug member material.

20. A lined valve assembly for medical applications comprising, in combination: a valve body member having a plurality of ports; a valve plug member; a liner generally interposed between said body member and said plug member; resilient raised portions on said liner for providing lines of sealing between said liner and said body member and for defining a flow path through the valve assembly; flute and spline means on said plug member and liner for providing sealing rigidity to said liner and for imparting generally simultaneous movement of both said liner and said plug member; said flow path being selectively positioned by movement of said plug member with respect to said body member; and means for assembling said plug member and said body member together.

21. The lined valve assembly of claim 20, wherein said flow path is defined by an indent within said liner; and said flute and spline means includes a generally transverse inside spline on said liner generally overlying said flow path indent, a generally transverse rear flute on said plug member generally overlying said generally transverse inside spline, a generally longitudinal spline on said liner, and a flute on said plug member generally overlying said generally longitudinal spline.

22. A device for medical applications, including a measuring chamber, a collection receptable in fluid-passing communication with said measuring chamber, and a valve assembly for controlling fluid flow between the measuring chamber and the collecting receptable, the improvement comprising said valve assembly including, in combination: a valve body member having a plurality of ports, a valve plug member, a liner generally interposed between said body member and said plug member, resilient means on said liner for providing lines of sealing between said liner and said body member and for defining a flow path through the valve assembly, said resilient means including a plurality of resilient raised portions on said liner, said flow path being selectively positioned by movement of said plug member with respect to said body member, and means for assembling said plug member and said body member together.

23. A device for medical applications, including a measuring chamber, a collection receptable in fluid passing communication with said measuring chamber, and a valve assembly for controlling fluid flow between the measuring chamber and the collection receptacle, the improvement comprising said valve assembly including, in combination: a valve body member having a plurality of ports, a valve plug member, a liner generally interposed between said body member and said plug member, resilient means on said liner for providing lines of sealing between said liner and said body member and for defining a flow path through the valve assembly, said flow path being selectively positioned by movement of said plug member with respect to said body member, and means for assembling said plug member and said body member together, wherein said valve assembly includes flute and spline means on said plug member and liner for providing sealing rigidity to said liner and for imparting generally simultaneous movement of said liner and said plug member.

24. The device of claim 23, wherein said flow path is defined by an indent with said liner; and said flute and spline means includes a generally transverse inside spline on said liner generally overlying said flow path indent, a generally transverse rear flute on said plug member generally overlying said generally transverse inside spline, a generally longitudinal spline on said liner, and a flute on said plug member generally overlying said generally longitudinal spline.

25. The device of claim 22, wherein said device is a urine drainage system, said measuring chamber is a semi-rigid enclosure within bound layers of resin film through which contents of the measuring chamber are visible, and said collection receptacle has generally flexible walls.

* * * * *